United States Patent
Reed et al.

(10) Patent No.: US 12,098,272 B2
(45) Date of Patent: Sep. 24, 2024

(54) HYDROGEL-ENZYME SYSTEMS AND METHODS

(71) Applicant: United States of America as Represented by The Secretary of The Army, Alexandria, VA (US)

(72) Inventors: Julian H Reed, Champaign, IL (US); Donald M Cropek, Champaign, IL (US)

(73) Assignee: UNITED STATES OF AMERICA AS REPRESENTED BY THE SECRETARY OF THE ARMY, Alexandria, VA (US)

( * ) Notice: Subject to any disclaimer, the term of this patent is extended or adjusted under 35 U.S.C. 154(b) by 0 days.

(21) Appl. No.: 17/397,967

(22) Filed: Aug. 9, 2021

(65) Prior Publication Data

US 2022/0049081 A1 Feb. 17, 2022

Related U.S. Application Data

(60) Provisional application No. 63/064,406, filed on Aug. 12, 2020.

(51) Int. Cl.
*C08L 33/10* (2006.01)
*C12N 9/16* (2006.01)

(52) U.S. Cl.
CPC ............... *C08L 33/10* (2013.01); *C12N 9/16* (2013.01); *C12Y 301/08001* (2013.01)

(58) Field of Classification Search
CPC .. C08L 33/10; C12N 9/16; C12N 9/86; C12N 9/96; C12N 11/087; C12Y 301/08001; C12Y 305/02006; A62D 2101/04; A62D 2203/02; A62D 3/02; A62D 3/40
See application file for complete search history.

(56) References Cited

FOREIGN PATENT DOCUMENTS

WO  WO 2017/017673 A9  *  2/2017  ............. C40B 30/02
WO  WO 2020/035865 A1  *  2/2020  ............. C12N 15/00

OTHER PUBLICATIONS

Banerjee et al., Improving enzymes for biomass conversion: A basic research perspective. Bioenerg. Res., 2010, vol. 3: 82-92. (Year: 2010).*
Basso et al., Hydrophobic microenvironment optimization for efficient immobilization of lipases on octadecyl functionalised resins. Tetrahedron, 2016, vol. 72: 7323-7328. (Year: 2016).*
Broun et al., Catalytic plasticity of fatty acid modification enzymes underlying chemical diversity of plant lipids. Science, 1998, vol. 282: 1315-1317. (Year: 1998).*
Campbell et al., Hydrogel-Immobilized Supercharged Proteins. Adv. Biosys., 2018, vol. 2, pp. 1-11. (Year: 2018).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Guo et al., Core/Shell Molecular Imprinting Microparticles Prepared Using RAFT Technology for Degradation of Paraoxon. Macromol. Res., 2011, vol. 19(11): 1202-1209. (Year: 2011).*
Khersonsky et al., Automated Design of Efficient and Functionally Diverse Enzyme Repertoires. Mol. Cell., 2018, vol. 72: 178-186. (Year: 2018).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Bigley et al., The evolution of phosphotriesterase for decontamination and detoxification of organophosphorus chemical warfare agents. Chemico-Biol., Interactions., 2019, vol. 308: 80-88. (Year: 2019).*
Cherny et al., Engineering V-Type Nerve Agents Detoxifying Enzymes Using Computationally Focused Libraries. ACS Chem. Biol., 2013, vol. 8: 2394-2403 (Year: 2013).*
Del Giudice et al., An Efficient Thermostable Organophosphate Hydrolase and its Application in Pesticide Decontamination. Biotechnol. Bioeng., 2015, vol. 113(4): 724-734 (Year: 2015).*

(Continued)

*Primary Examiner* — Ganapathirama Raghu
(74) *Attorney, Agent, or Firm* — Brian C. Jones

(57) ABSTRACT

In one embodiment, a hydrogel-enzyme construct for performing high temperature enzymatic reaction on paraoxon, and/or for performing enzymatic reaction on paraoxon following exposure to high temperature, includes a hydrogel having multiple layers of poly(methacrylic acid) (PMAA) and a plurality of dPTE2 enzyme molecules. Individual dPTE2 enzyme molecules are embedded between adjacent PMAA layers and are covalently bonded with respective individual PMAA layers. The hydrogel-enzyme construct is capable of performing enzymatic reaction on the paraoxon when the paraoxon is exposed to the hydrogel-enzyme construct under a temperature condition of up to above 99° C. and below 100° C. or when the paraoxon is exposed to the hydrogel-enzyme construct after the hydrogel-enzyme construct has been heated to a temperature condition of up to 550° C., where the enzymatic reaction on the paraoxon by individual dPTE2 molecules embedded within the hydrogel occurs at a residual activity of between 20% and 100%.

15 Claims, 13 Drawing Sheets
Specification includes a Sequence Listing.

(56) References Cited

OTHER PUBLICATIONS

Goldenzweig et al., Automated Structure- and Sequence-Based Design of Proteins for High Bacterial Expression and Stability. Mol. Cell., 2016, vol. 63: 337-346 (Year: 2016).*

Kozlovskaya et al., Architecture of Hydrated Multilayer Poly(methacrylic acid) Hydrogels: The Effect of Solution pH. ACS Appl. Polym. Mater., 2020, vol. 2: 2260-2273. (Year: 2020).*

Suthiwangcharoen et al., Enhancing Enzyme Stability by Construction of Polymer-Enzyme Conjugate Micelles for Decontamination of Organophosphate Agents. Biomacromol., 2014, vol. 15: 1142-112. (Year: 2014).*

\* cited by examiner

SEQUENCE LISTING

```
<160> NUMBER OF SEQ ID NOS: 1

<210> SEQ ID NO 1
<211> LENGTH: 7642
<212> TYPE: DNA
<213> ORGANISM: Artificial Sequence
<220> FEATURE:
<223> OTHER INFORMATION: dPTE2 (PROSS Stabilized PTE S5)

<400> SEQUENCE: 1
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta aatctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatctcggta gtgggatacg     900
acgataccga agacagctca tgttatatcc cgccgttaac caccatcaaa caggattttc     960
gcctgctggg gcaaaccagc gtggaccgct tgctgcaact ctctcagggc caggcggtga    1020
```

```
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcacttcacc aacaaggacc atagcatatg aaaatcgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt ggtggctac    1740 gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta aacaaagat ctgctgccga acccgccaaa aacctgggaa    1920
gagatcccgg cgctggataa agaactgaaa gcgaaggta gagcgcgct gatgttcaac    1980 ctgcaagaac cgtacttcac ctggccgctg attgctgctg acggggggtta tgcgttcaag    2040 tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccact atggaaaacg cccagaaagg tgaaatcatg    2520
ccgaacatcc cgcagatgtc cgcttcctgg tatgccgtgc gtactgcggt gatcaacgcc    2580
gccagcggtc gtcagactgt cgatgaagcc ctgaaagacg cgcagactaa ttcgagctcg    2640
aacaacaaca acaataacaa taacaacaac ctcgggatcg agggaaggat ttcagaattc    2700
atcaccaaca gcggcgaccg tatcaacacc gttcgtggtc cgatcaccat ctctgaggcc    2760
ggtttcactc tgatgcatga gcatatctgc ggttcttctg cgggtttct ccgcgcttgg    2820 ccggagttct tcggttcccg tgatgcactg gcggaaaaag cggttcgcgg cctccgtcgc    2880
gctcgtgctg ccggcgttcg taccatcgtt gatgtttcta cctttgatat cggccgtgac    2940
gttgagctgc tcgccgaagt ttctgaagcg gcggacgttc acatcgtcgc ggcgacgggt    3000
ctgtggttcg acccgcctct gtctatgcgc ctgcgttctg ttgaggaact cacccagttc    3060
tttctgcgcg aaatccagta cggtatcgag gataccggca tccgtgcagg tatcatcaaa    3120
gttgcgacca ccggtaaagc cacgccgttc caggagcgtg tactccgtgc ggctgcacgc    3180
gcctctctcg cgaccggtgt gcctgttacc acccataccg atgcttctca gcgtgacggt    3240
gagcagcagg cggacatctt cgaatctgaa ggcctcgatc cgagccgtgt ttgcattggt    3300
cattctgacg acaccgacga cctggactac ctgaccgctc tcgcagctcg cggttatctg    3360
attggtctgg atcacattcc gcacagcgcg atcggcctgg aagacaacgc gtccgctgcc    3420
```

```
gcgctgctgg gcctgcgctc ttggcaaacc cgtgccctcc tgatcaaagc gctgatcgac    3480
cagggctacg ccgaccagat cctggtttct aacgactggc tgttcggttt ctcttcttac    3540
gttaccaaca tcatggatgt catggaccgt gttaacccgg atggtatggc gttcatccct    3600
ctgcgtgtta ttccattcct ccgtgaaaaa ggtgttccgg acgagactct cgaaacgatc    3660
atggttgaca acccagctcg tttcctgtct ccgaccctgc gtgcgagctg ataactgcag    3720
gcaagcttgg cactggccgt cgttttacaa cgtcgtgact gggaaaaccc tggcgttacc    3780
caacttaatc gccttgcagc acatccccct ttcgccagct ggcgtaatag cgaagaggcc    3840
cgcaccgatc gcccttccca cagttgcgc agcctgaatg gcgaatggca gcttggctgt    3900
tttggcggat gagataagat tttcagcctg atacagatta aatcagaacg cagaagcggt    3960
ctgataaaac agaatttgcc tggcggcagt agcgcggtgg tcccacctga ccccatgccg    4020
aactcagaag tgaaacgccg tagcgccgat ggtagtgtgg ggtctcccca tgcgagagta    4080
gggaactgcc aggcatcaaa taaaacgaaa ggctcagtcg aaagactggg cctttcgttt    4140
tatctgttgt ttgtcggtga acgctctcct gagtaggaca atccgccgg gagcggattt    4200 gaacgttgcg aagcaacggc ccggagggtg cgggcagga cgcccgccat aaactgccag    4260
gcatcaaatt aagcagaagg ccatcctgac ggatggcctt tttgcgtttc tacaaactct    4320
ttttgtttat ttttctaaat acattcaaat atgtatccgc tcatgagaca ataaccctga    4380
taaatgcttc aataatattg aaaaggaag agtatgagta ttcaacattt ccgtgtcgcc    4440
cttattccct tttttgcggc attttgcctt cctgttttttg ctcacccaga acgctggtg    4500 aaagtaaaag atgctgaaga tcagttgggt gcacgagtgg gttacatcga actggatctc    4560
aacagcggta agatccttga gttttcgc cccgaagaac gttctccaat gatgagcact    4620
tttaaagttc tgctatgtgg cgcggtatta tcccgtgttg acgccgggca agagcaactc    4680
ggtcgccgca tacactattc tcagaatgac ttggttgagt actcaccagt cacagaaaag    4740
catcttacgg atggcatgac agtaagagaa ttatgcagtg ctgccataac catgagtgat    4800
aacactgcgg ccaacttact tctgacaacg atcggaggac cgaaggagct aaccgctttt    4860
ttgcacaaca tgggggatca tgtaactcgc cttgatcgtt gggaaccgga gctgaatgaa    4920
gccataccaa acgacgagcg tgacaccacg atgcctgtag caatggcaac aacgttgcgc    4980
aaactattaa ctggcgaact acttactcta gcttcccggc aacaattaat agactggatg    5040
gaggcggata agttgcagg accacttctg cgctcggccc ttccggctgg ctggtttatt    5100
gctgataaat ctggagccgg tgagcgtggg tctcgcggta tcattgcagc actggggcca    5160
gatggtaagc cctcccgtat cgtagttatc tacacgacgg ggagtcaggc aactatggat    5220
gaacgaaata gacagatcgc tgagataggg gcctcactga ttaagcattg gtaactgtca    5280
gaccaagttt actcatatat actttagatt gatttacccc ggttgataat cagaaaagcc    5340
ccaaaaacag aagattgta taagcaaata tttaaattgt aaacgttaat attttgttaa    5400
aattcgcgtt aaattttgt taaatcagct cattttttaa ccaataggcc gaaatcggca    5460 aaatcccta taaatcaaaa gaatagaccg agataggggtt gagtgttgtt ccagtttgga    5520
acaagagtcc actattaaag aacgtggact ccaacgtcaa agggcgaaaa accgtctatc    5580
agggcgatgg cccactacgt gaaccatcac ccaaatcaag ttttttgggg tcgaggtgcc    5640
gtaaagcact aaatcggaac cctaaaggga gccccgatt tagagcttga cggggaaagc    5700
cggcgaacgt ggcgagaaag gaagggaaga agcgaaagg agcgggcgct agggcgctgg    5760
```

```
caagtgtagc ggtcacgctg cgcgtaacca ccacacccgc cgcgcttaat gcgccgctac    5820
agggcgcgta aaaggatcta ggtgaagatc cttttttgata atctcatgac caaaatccct   5880
taacgtgagt tttcgttcca ctgagcgtca gacccccgtag aaaagatcaa aggatcttct   5940
tgagatcctt ttttctgcg cgtaatctgc tgcttgcaaa caaaaaaacc accgctacca    6000
gcggtggttt gtttgccgga tcaagagcta ccaactcttt ttccgaaggt aactggcttc   6060
agcagagcgc agataccaaa tactgtcctt ctagtgtagc cgtagttagg ccaccacttc   6120
aagaactctg tagcaccgcc tacatacctc gctctgctaa tcctgttacc agtggctgct   6180
gccagtggcg ataagtcgtg tcttaccggg ttggactcaa gacgatagtt accggataag   6240
gcgcagcggt cgggctgaac ggggggttcg tgcacacagc ccagcttgga gcgaacgacc   6300
tacaccgaac tgagatacct acagcgtgag ctatgagaaa gcgccacgct tcccgaaggg   6360
agaaaggcgg acaggtatcc ggtaagcggc agggtcggaa caggagagcg cacgagggag   6420
cttccagggg gaaacgcctg gtatctttat agtcctgtcg ggtttcgcca cctctgactt   6480
gagcgtcgat ttttgtgatg ctcgtcaggg gggcggagcc tatggaaaaa cgccagcaac   6540
gcggcctttt tacggttcct ggccttttgc tggccttttg ctcacatgtt ctttcctgcg   6600
ttatcccctg attctgtgga taaccgtatt accgcctttg agtgagctga taccgctcgc   6660
cgcagccgaa cgaccgagcg cagcgagtca gtgagcgagg aagcggaaga gcgcctgatg   6720
cggtattttc tccttacgca tctgtgcggt atttcacacc gcatatatgg tgcactctca   6780
gtacaatctg ctctgatgcc gcatagttaa gccagtatac actccgctat cgctacgtga   6840
ctgggtcatg gctgcgcccc gacacccgcc aacacccgct gacgcgccct gacgggcttg   6900
tctgctcccg gcatccgctt acagacaagc tgtgaccgtc tccgggagct gcatgtgtca   6960
gaggttttca ccgtcatcac cgaaacgcgc gaggcagctg cggtaaagct catcagcgtg   7020
gtcgtgcagc gattcacaga tgtctgcctg ttcatccgcg tccagctcgt tgagtttctc   7080
cagaagcgtt aatgtctggc ttctgataaa gcgggccatg ttaagggcgg ttttttcctg   7140
tttggtcact gatgcctccg tgtaaggggg atttctgttc atgggggtaa tgataccgat   7200
gaaacgagag aggatgctca cgatacgggt tactgatgat gaacatgccc ggttactgga   7260
acgttgtgag ggtaaacaac tggcggtatg gatgcggcgg gaccagagaa aaatcactca   7320
gggtcaatgc cagcgcttcg ttaatacaga tgtaggtgtt ccacagggta gccagcagca   7380
tcctgcgatg cagatccgga acataatggt gcagggcgct gacttccgcg tttccagact   7440
ttacgaaaca cggaaaccga agaccattca tgttgttgct caggtcgcag acgttttgca   7500
gcagcagtcg cttcacgttc gctcgcgtat cggtgattca ttctgctaac cagtaaggca   7560
acccccgccag cctagccggg tcctcaacga caggagcacg atcatgcgca cccgtggcca   7620
ggacccaacg ctgcccgaaa tt                                            7642
```

HYDROGEL-ENZYME SYSTEMS AND METHODS

CROSS-REFERENCE TO RELATED APPLICATIONS

The application is a nonprovisional of and claims the benefit of priority from U.S. Patent Application No. 63/064,406, filed on Aug. 12, 2020, entitled HYDROGEL-ENZYME SYSTEMS AND METHODS, the disclosure of which is incorporated by reference in its entirety.

STATEMENT OF GOVERNMENT INTEREST

Under paragraph 1(a) of Executive Order 10096, the conditions under which this invention was made entitle the Government of the United States, as represented by the Secretary of the Army, to an undivided interest therein on any patent granted thereon by the United States. This and related patents are available for licensing to qualified licensees.

BACKGROUND

Field of the Invention

The present invention relates to enzyme compositions, and, more particularly but not exclusively, to hydrogel-enzyme constructs that retain catalytic activity following exposure to very high temperature and/or very low moisture conditions, and to chemical denaturants. In some cases, hydrogel-enzyme constructs can perform catalytic activity not only above their normal temperature bound, but also following extensive heating and desiccation. The hydrogel-enzyme constructs can also perform catalytic activity in the presence of high concentrations of a chemical denaturant.

Description of the Related Art

This section introduces aspects that may help facilitate a better understanding of the invention. Accordingly, the statements of this section are to be read in this light and are not to be understood as admissions about what is prior art or what is not prior art.

Enzymes provide the biological backbone through which catalytic reactions occur and allow life to exist. Various classes of enzymes exist, such as oxidoreductases, transferases, hydrolases, isomerases, and the like. Millions of annotations on enzymatic occurrence, function, kinetics, and molecular properties exist on the BRaunschweig ENzyme DAtabase (BRENDA). Organisms, and their corresponding enzymes, can be grouped into four primary categories based on the temperature range they grow in: psychrophiles (−20-10° C.), mesophiles (20-45° C.), thermophiles (40-80° C.), and hyperthermophiles (80-115° C.). Within BRENDA, the highest currently reported temperature optimum for an enzyme is 125° C. for the S-methyl-5'-thioadenosine phosphorylase of the hyperthermophilic archaeon Pyrococcus furiosus, with a melting temperature of 137-139° C. Given such enzymes' stability at higher temperatures, understanding this phenomenon has driven great interest for both fundamental knowledge of enzyme structure-function relationships, especially for use outside the enzyme's normal operational temperature range, including elevated temperature applications in biomanufacturing and industry.

Numerous enzymes which possess high thermal, pH, and/or detergent stabilities have found use in various commercial processes. For instance, fused xylanases from fungi and actinomycetes have been used in the paper and pulp industries due to their high thermal and pH stabilities. One particularly appropriate example of the importance of extremophilic enzymes in industrial applications is the conversion of starch into single glucose units. In this process, liquefaction of raw starch is achieved at temperatures −100° C. for 1 h, then saccharification at 60° C. for 3 h. Unfortunately, commonly used enzymes in the production of glucose are not active at high temperatures, necessitating temperature adjustments, which increases energy and time requirements. Fortunately, more suitable extremophilic amylolytic enzymes have helped to optimize this procedure. Various other industrial processes could benefit from developing a way to improve enzyme stability from thermal, pH, detergent, or other challenges.

A number of different approaches have been taken in an attempt to increase the functional temperature range of various enzymes, with varying levels of success. Protein engineering is a common method by which improved thermostability is achieved. Approaches include rational site-directed, random, or, recently, computationally guided mutagenesis. The introduction of additional structural features, such as salt bridges, has also been shown to improve thermostability. Beyond noncovalent interactions, designed disulfide bonds are a well-developed means of improving thermostability. Overall, the manipulation and design of specific forces, such as hydrophobic and electrostatic interactions, hydrogen bonds, and even covalent bonds within the enzyme scaffold can confer and improve thermostability.

Although existing enzyme stability approaches may provide value in certain situations, still further improvements in enhancing enzyme performance following exposure to very high temperatures or very dry conditions or chemical denaturants are desired. Embodiments of the present invention provide solutions for at least some of these outstanding needs.

SUMMARY

The present invention was developed to address the challenges associated with existing enzyme systems and methods. Exemplary embodiments disclosed herein provide hydrogel-enzyme constructs that can perform catalytic activity following exposure to very high temperatures. Hydrogel-enzyme constructs may include enzymes such as dPTE2, β-lactamase, and the like.

A hydrogel according to embodiments of the present invention can be constructed to have multiple linked layers of compounds or chemicals. A hydrogel can effectively provide a semi-aqueous environment suitable for supporting the biological activity of one or more enzymes embedded therein. Hydrogel-enzyme constructs disclosed herein include hydrogels having embedded enzymes, wherein the enzymes within the hydrogel matrices exhibit catalytic activity above their normal temperature bound, and following exposure to extremely high temperature and desiccating conditions. Further, the enzymes embedded within the hydrogel are also resistant to chemical denaturants. Embodiments of the present invention encompass hydrogel constructs that exhibit extraordinary enzymatic temperature denaturation tolerance within poly(methacrylic acid) (PMAA) hydrogels. It is believed that hydrogels such as PMAA hydrogels may function as thermo-protectants for enzymes, allowing them to perform catalytic activity above their normal temperature bound, and following exposure to extremely high temperature and desiccating conditions. The hydrogels may function as chemo-protectants for enzymes, allowing them to perform catalytic activity following or together with exposure to a chemical denaturant such as urea.

In accordance with an aspect, a method of performing enzymatic reaction on paraoxon comprises: providing a hydrogel-enzyme construct, the construct comprising a hydrogel having multiple layers of poly(methacrylic acid) (PMAA) and a plurality of dPTE2 enzyme molecules, wherein adjacent PMAA layers are connected via ethylenediamine cross-linking, wherein individual dPTE2 enzyme molecules are embedded between adjacent PMAA layers, and wherein individual dPTE2 molecules are covalently bonded with respective individual PMAA layers; exposing the hydrogel-enzyme construct to a high temperature condition of up to 550° C.; and exposing the paraoxon to the hydrogel-enzyme construct following the high temperature exposure step. Enzymatic reaction on the paraoxon by individual dPTE2 molecules embedded within the hydrogel occurs at a residual activity of between 20% and 100%.

In some embodiments, the high temperature condition is between about 40° C. and about 450° C. and the residual activity is between about 64% and about 100%.

In accordance with another aspect, a method of performing high temperature enzymatic reaction on a reactant comprises: providing a hydrogel-enzyme construct, the construct comprising a hydrogel having multiple layers of a hydrogel polymer and a plurality of enzyme molecules, wherein adjacent hydrogel polymer layers are connected via cross-linking, wherein individual enzyme molecules are embedded between adjacent hydrogel polymer layers, and wherein individual enzyme molecules are covalently bonded with respective individual hydrogel polymer layers; exposing the hydrogel-enzyme construct to a high temperature condition of up to 550° C.; and exposing the reactant to the hydrogel-enzyme construct following the high temperature exposure step. Enzymatic reaction on the reactant by individual enzyme molecules embedded within the hydrogel occurs at a residual activity of between 20% and 100%.

In specific embodiments, the hydrogel polymer comprises poly(methacrylic acid) (PMAA). The reactant may be an organophosphate, such as paraoxon. The plurality of enzyme molecules may comprise phosphotriesterase molecules, such as dPTE2 molecules or other enzymes, such as β-lactamase. The adjacent hydrogel polymer layers may be connected via ethylenediamine cross-linking.

In accordance with another aspect, a hydrogel-enzyme construct for performing high temperature enzymatic reaction on paraoxon comprises: a hydrogel having multiple layers of poly(methacrylic acid) (PMAA) and a plurality of dPTE2 enzyme molecules. Adjacent PMAA layers are connected via ethylenediamine cross-linking. Individual dPTE2 enzyme molecules are embedded between adjacent PMAA layers. Individual dPTE2 molecules are covalently bonded with respective individual PMAA layers. The hydrogel-enzyme construct is capable of performing enzymatic reaction on the paraoxon after the hydrogel-enzyme construct is exposed to a high temperature condition of up to 550° C., the enzymatic reaction on the paraoxon by individual dPTE2 molecules embedded within the hydrogel occurring at a residual activity of between 20% and 100%.

In accordance with another aspect, a hydrogel-enzyme construct for performing high temperature enzymatic reaction on a reactant comprises: a hydrogel having multiple layers of a hydrogel polymer and a plurality of enzyme molecules. Adjacent hydrogel polymer layers are connected via cross-linking. Individual enzyme molecules are embedded between adjacent hydrogel polymer layers. Individual enzyme molecules are covalently bonded with respective individual hydrogel polymer layers. The hydrogel-enzyme construct is capable of performing enzymatic reaction on the reactant after the hydrogel-enzyme construct is exposed to a high temperature condition of up to 550° C., the enzymatic reaction on the reactant by individual enzyme molecules embedded within the hydrogel occurring at a residual activity of between 20% and 100%.

In accordance with another aspect, a method of performing high temperature enzymatic reaction on paraoxon comprises: providing a hydrogel-enzyme construct, the construct comprising a hydrogel having multiple layers of poly(methacrylic acid) (PMAA) and a plurality of dPTE2 enzyme molecules, wherein adjacent PMAA layers are connected via ethylenediamine cross-linking, wherein individual dPTE2 enzyme molecules are embedded between adjacent PMAA layers, and wherein individual dPTE2 molecules are covalently bonded with respective individual PMAA layers; and exposing the paraoxon to the hydrogel-enzyme construct under a temperature condition of up to above 99° C. and below 100° C.

In accordance with another aspect, a method of performing high temperature enzymatic reaction on a reactant comprises: providing a hydrogel-enzyme construct, the construct comprising a hydrogel having multiple layers of a hydrogel polymer and a plurality of enzyme molecules, wherein adjacent hydrogel polymer layers are connected via cross-linking, wherein individual enzyme molecules are embedded between adjacent hydrogel polymer layers, and wherein individual enzyme molecules are covalently bonded with respective individual hydrogel polymer layers; and exposing the reactant to the hydrogel-enzyme construct under a temperature condition of up to above 99° C. and below 100° C.

In accordance with another aspect, a hydrogel-enzyme construct for performing high temperature enzymatic reaction on paraoxon comprises: a hydrogel having multiple layers of poly(methacrylic acid) (PMAA) and a plurality of dPTE2 enzyme molecules. Adjacent PMAA layers are connected via ethylenediamine cross-linking. Individual dPTE2 enzyme molecules are embedded between adjacent PMAA layers. Individual dPTE2 molecules are covalently bonded with respective individual PMAA layers. The hydrogel-enzyme construct is capable of performing enzymatic reaction on the paraoxon when the paraoxon is exposed to the hydrogel-enzyme construct under a temperature condition of up to above 99° C. and below 100° C.

In accordance with another aspect, a hydrogel-enzyme construct for performing high temperature enzymatic reaction on a reactant comprises: a hydrogel having multiple layers of a hydrogel polymer and a plurality of enzyme molecules. Adjacent hydrogel polymer layers are connected via cross-linking. Individual enzyme molecules are embedded between adjacent hydrogel polymer layers. Individual enzyme molecules are covalently bonded with respective individual hydrogel polymer layers. The hydrogel-enzyme construct is capable of performing enzymatic reaction on the reactant when the reactant is exposed to the hydrogel-enzyme construct under a temperature condition of up to above 99° C. and below 100° C.

The present invention advances the science of enzyme systems and methods. This disclosure describes a new hydrogel-enzyme system and methods that are more effective than prior approaches. For example, the instant hydrogel-enzyme systems can be used to catalyze useful enzymatic reactions at high temperatures, and following exposure to very high temperatures and desiccating conditions, as well as after exposure to chemical denaturants.

BRIEF DESCRIPTION OF THE DRAWINGS

Embodiments of the invention will become more fully apparent from the following detailed description, the appended claims, and the accompanying drawings in which like reference numerals identify similar or identical elements.

DETAILED DESCRIPTION

Detailed illustrative embodiments of the present invention are disclosed herein. However, specific structural and functional details disclosed herein are merely representative for purposes of describing example embodiments of the present invention. The present invention may be embodied in many alternate forms and should not be construed as limited to only the embodiments set forth herein. Further, the terminology used herein is for the purpose of describing particular embodiments only and is not intended to be limiting of example embodiments of the invention.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

In at least one embodiment, hydrogel-enzyme systems and methods disclosed herein provide constructs that can perform catalytic activity under very high temperature conditions.

Figure 1:
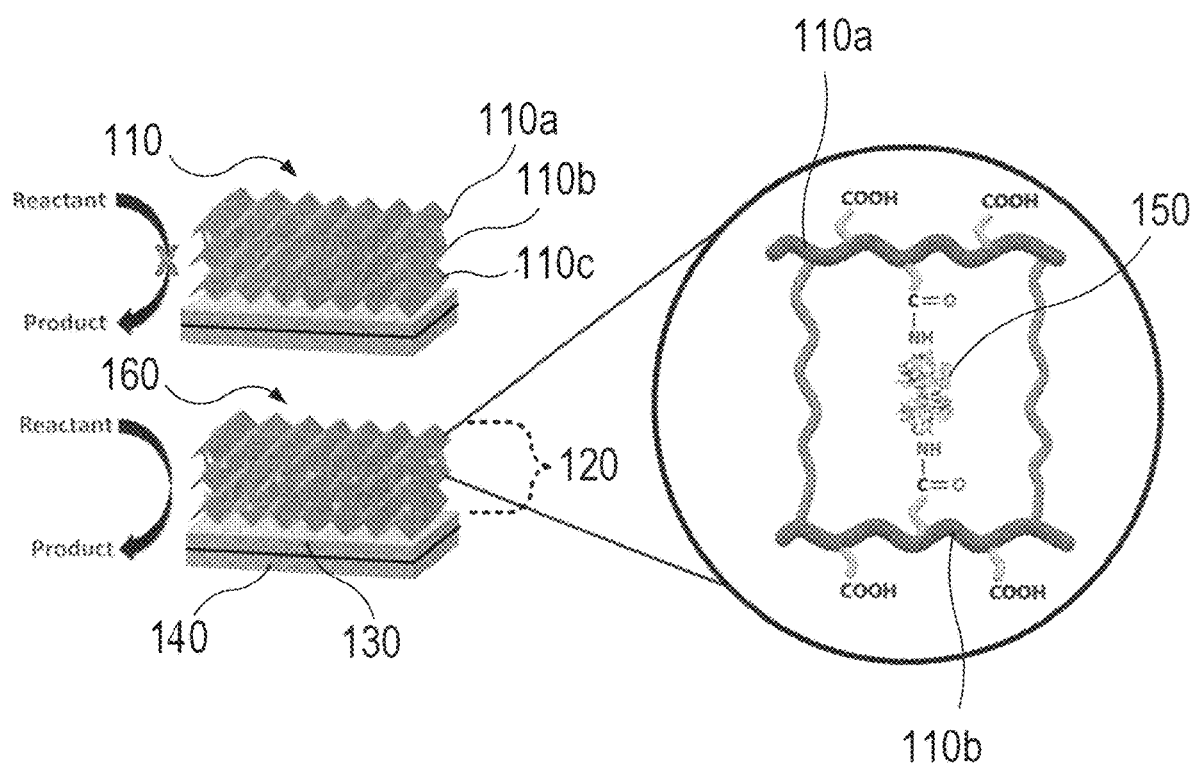
FIG. 1 depicts aspects of a hydrogel-enzyme system according to certain embodiments of the invention.

Turning now to the drawings, FIG. 1 depicts aspects of an exemplary hydrogel-enzyme construct or system for use in embodiments of the present invention. As shown here, a hydrogel 110 includes layers (110a, 110b, 110c) of poly (methacrylic acid) (PMAA). A hydrogel 110 can be combined with an enzyme 150 to produce a hydrogel-enzyme construct 160. Hydrogel 110 does not perform to convert a reactant to a product. Hydrogel-enzyme construct 160 performs to convert a reactant to a product. A hydrogel 110 may include carboxyl groups (—COOH) that become linked to an enzyme 150. As shown here, multiple layers of PMAA (110a, 110b, 110c) form a PMAA layer composite 120 which is a structural representation of the hydrogel 110. The PMAA layer composite 120 (hydrogel 110) is in contact with a layer of poly(glycidyl methacrylate) (PGMA) 130. In turn, the PGMA layer 130 is in contact with a silicon wafer 140. According to some embodiments, a silicon wafer 140 can have a thin layer of silicon oxide on the surface thereof, containing —OH groups, which operate as anchors to help keep the PGMA layer 130 secured to the silicon wafer 140. In some cases, the PGMA layer is present as a monolayer. In some cases, the PMAA layer composite 120 (hydrogel 110) is secured to the PGMA layer via covalent bonding.

To prepare a hydrogel as a multilayer film construction, polymers (e.g., poly(methacrylic acid)) were dissolved in deionized (DI) water and deposited from 1 mg/mL aqueous polymer solutions using a spin-assisted layer-by-layer (spin-LBL) technique. In some cases, a phosphate buffer may be added to the polymer and water. Embodiments of the present invention encompass the use of spin coating and other techniques for creating multilayer hydrogels.

Prior to a hydrogen-bonded multilayer deposition, the silicon wafers were cleaned. The layer of PGMA was spin-cast from a 0.1 mg/mL chloroform solution onto the surface of the Si wafer, followed by heating at 110° C. for 1 h and rinsing with chloroform. A PMAA layer was then adsorbed on the PGMA-primed wafers from a 1 mg/mL methanol solution and cross-linked at 100° C. for 40 min, followed by rinsing with DI water. (PMAA/PVPON)$_n$ LBL films were deposited on the precursor-coated wafers. Briefly, 3 mL of poly(methacrylic acid) (PMAA) or poly(vinylpyrrolidone) PVPON solutions in 0.01 M phosphate buffer at pH=2.5 were alternately dropped onto PGMA-PMAA primed silicon substrates, rotated for 30 s at 3000 rpm on a spin-coater, and then rinsed twice for 30 s with the buffer solution before the deposition of the next layer. To produce the hydrogels, PMAA layers within the H-bonded multilayers were chemically cross-linked. Briefly, the films were exposed to 1-ethyl-3-(3-dimethylaminopropyl)carbodiimide hydrochloride (EDC) solution (5 mg/mL, pH=5.0, 0.01 M phosphate buffer) for 40 min, followed by cross-linking with ethylenediamine (EDA) (5 mg/mL, 0.01 M phosphate buffer, pH=5.8) for 16 h. After that, the cross-linked PMAA hydrogel films were submerged into buffer solutions at pH=8.0 (0.01 M phosphate buffer) for 24 h to remove PVPON, followed by deswelling of the films in 0.01 M phosphate buffer at pH=5 (15 min) and drying at ambient conditions. Additional aspects of hydrogel fabrication methods are discussed in Kozlovskaya et al, *Controlling Internal*

*Organization of Multilayer Poly(methacrylic acid) Hydrogels with Polymer Molecular Weight, Macromolecules* 48, 8585-8593 (2015), the content of which is incorporated herein by reference.

Hence, it can be understood that at one stage in the hydrogel preparation process, the construct includes alternating PMAA and PVPON layers, and this construct is soaked in a solution containing cross-linkers, after which the PMAA layers become connected via cross-linking. The construct can then be soaked in a solution that dissolves away the PVPON sacrificial layers, leaving the cross-linked PMAA layers (e.g., layers 262A and cross-linkers 264A in FIG. 2). In some instances, the hydrogel 260A is a hydrogen bonded hydrogel.

According to some embodiments, a PVPON layer that is sandwiched between adjacent PMAA layers can function as a sacrificial layer. The PMAA layers can have a slight negative charge, and the PVPON layers can have a slight positive charge. This difference in charge can provide electrostatic attraction between PMAA and PVPON layers that contact one another. In addition or in place of spin-casting, other methods may be used to construct a hydrogel.

Figure 2:
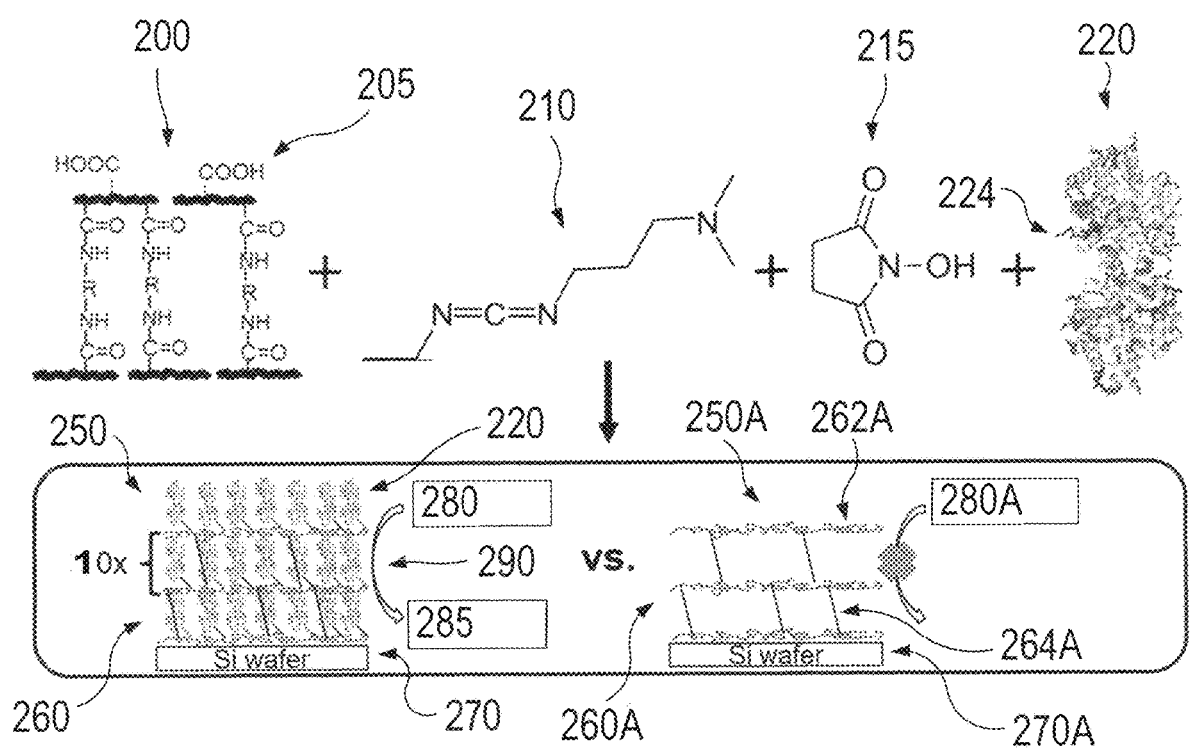
FIG. 2 illustrates aspects of a hydrogel-enzyme system according to certain embodiments of the invention.

FIG. 2 depicts aspects of a process for embedding an enzyme 220 in a hydrogel 200 (e.g., PMAA hydrogel), according to embodiments of the present invention. As shown here, carboxyl groups (—COOH) 205 of a hydrogel 200 can be exposed to 1-ethyl-3-(3-dimethylaminopropyl) carbodiimide hydrochloride (EDC) 210 and N-hydroxysuccinimide (NHS) 215, which enhances binding or coupling between the carboxyl groups 205 of the hydrogel 200 and amines of the enzyme 220, including Lys residues 224, and the N-terminus. The N terminus, arginine, lysine, asparagine, glutamine all have potential amine binding sites. In some embodiments, arginine, asparagine, and glutamine are not appropriate bases for this reaction (guanidine group and oxyamine, respectively). In some embodiments, Lys and N-terminal are appropriate (primary amine). According to some embodiments, the enzyme 220 becomes covalently linked with the hydrogel 200. According to some embodiments, carboxyl functional groups 205 attached to or associated with a PMAA hydrogel 200 are capable of covalently conjugating peptides or proteins via carbodiimide crosslinker chemistry, facilitated by EDC ((1-ethyl-3-(3-dimethylaminopropyl)carbodiimide hydrochloride) 210 and NHS (N-hydroxysuccinimide) 215. According to some embodiments, COOH groups in the enzyme can covalently bind to free amine groups from the EDA crosslinker. According to some embodiments, COOH groups in the system bind to $NH_2$ groups in the system where system includes both hydrogel and enzyme.

In exemplary experiments, the dPTE2 was obtained from a plasmid (e.g., Addgene plasmid #111634) SEQ ID NO: 1). In some cases, dPTE2 was buffer exchanged into 100 mM Tris pH 8.0, 100 mM NaCl, and 100 μM $ZnCl_2$ using a PD-10 column containing Sephadex G-25.

According to some embodiments, poly(methacrylic acid) (PMAA, Mw 100,000 g/mol) and poly(N-vinylpyrrolidone) (PVPON, Mw 58,000 g/mol) can be used to fabricate a hydrogel, along with ethylenediamine (EDA), ((1-ethyl-3-(3-dimethylaminopropyl)carbodiimide hydrochloride) (EDC), and sodium monobasic and sodium dibasic phosphate buffers. In some cases, water can be of ultrapure quality (minimum resistivity 18.2 MΩ.cm).

Exemplary multilayer PMAA hydrogel coatings (e.g., 20 layers of PMAA denoted as $(PMAA)_{20}$) were prepared using spin-assisted self-assembly of PMAA and PVPON via hydrogen-bonding. The multilayer coating was prepared from 0.5 mg/mL polymer solutions (0.01 M phosphate buffer, pH=2.5) using a Laurell spin-coater at 2000 rpm. The polymer excess was removed after each deposited polymer layer using a rinsing buffer solution (0.01 M phosphate buffer, pH=2.5). After a desired number of PMAA/PVPON bilayers were adsorbed, the multilayer was crosslinked with ethylenediamine for 16 hours using carbodiimide-assisted chemistry. After crosslinking, the obtained hydrogel coating was exposed to pH=8 (0.01 M phosphate buffer) for 24 hours to release PVPON, followed by two rinses in 0.01 M phosphate buffer at pH=5, and dried with a low stream of nitrogen.

The hydrogel construct 250, which includes a $(PMAA)_{20}$ hydrogel 260 on a Silicon wafer 270, incorporates a plurality of enzymes 220 on and throughout the hydrogel 260. The hydrogel construct 250 is effective in converting a reactant 280 to a product 285 by virtue of an enzymatic reaction 290 catalyzed by the enzymes 220. According to some embodiments, the structure of enzyme 220 can be further understood with reference to Protein Data Bank (PDB) identification code 1 DPM (phosphotriesterase). In some embodiments, the enzyme 220 is a homolog of Protein Data Bank (PDB) identification code 1 DPM (phosphotriesterase). In some cases, the enzyme 220 is a Zn-containing phosphotriesterase from the organism *Brevundimonas diminuta*. In some cases, the enzyme 220 is a mutant form of a Zn-utilizing phosphotriesterase from the organism *Pseudomonas diminuta*.

Enzymatic reaction includes the broadest sense of building new molecular species from a chemical substrate or degradation of the chemical substrate. The experiments described in this disclosure involve enzymatic degradation. Without being bound by any particular theory, it is believed that enzymatic building, where construction or synthesis of new molecules is desired, can be observed in other experiments different from those reported in this disclosure.

By comparison, it can be seen that a hydrogel construct 250A that includes a hydrogel 260A and a Silicon wafer 270A, without enzymes, is not effective in converting the reactant 280A to a product. Hence, the presence of enzyme 220 is necessary to observe a desired reaction 290. As shown here, hydrogel 260A includes multiple PMAA layers 262A which are connected via crosslinkers 264A. The enzyme-infused hydrogel 260 includes similar layers and cross-linkers, although they are not labeled in this drawing.

Although the hydrogel 260 depicted in FIG. 2 is a 20 layer hydrogel, it is understood that embodiments of the present invention encompass the use of hydrogels having any desired number of layers. For example, the hydrogel may include 20 layers, lesser than 20 layers, or more than 20 layers. In some cases, a hydrogel may include 40 layers, 50 layers, 60 layers, and the like. As shown here, the layers 262A are separated by a certain distance, for example the distance between adjacent layers can be defined by a space therebetween. It is also understood that hydrogel preparation methods may involve different materials and/or different methods steps so as to result in hydrogels having layers that are separated by a desired distance. By selectively choosing such a mesh size or matrix spacing, it is possible to provide hydrogels wherein any of a variety of differently sized enzymes can be embedded therein.

According to some embodiments, the hydrogel 260 can be placed or constructed on the Silicon wafer 270 prior to embedding the enzyme 220 in the hydrogel 260. As shown here, in some embodiments, enzyme molecules 220 can be embedded throughout the entirety of the hydrogel 260 and can also be attached within or displayed on the surfaces of the hydrogel 260. Hence, reactant 280 that contacts the hydrogel 260 or that diffuses through the hydrogel 260 (e.g., via pores or matrix interstices of the hydrogel) can come into contact with the enzyme 220, such that a reaction 290 ensues.

According to some embodiments, a hydrogel-enzyme system which includes enzyme 220 embedded in a hydrogel 260 can provide enhanced thermostability to the functionality of the enzyme 220. In some embodiments, the enzyme thermostability of the embedded enzyme is influenced by the thermostability of the hydrogel. In some embodiments, the enzyme thermostability of the embedded enzyme is directly related to the thermostability of the hydrogel. In some embodiments, the hydrogel can play a protective role for the enzyme upon incorporation of the enzyme therein.

In exemplary experiments, the coupling of enzymes to the $(PMAA)_{20}$ hydrogels or the incorporation or embedding of the enzymes into the hydrogels was accomplished using EDC (1-ethyl-3-(3-dimethylaminopropyl)carbodiimide hydrochloride)-NHS (N-hydroxysuccinimide) coupling. In this reaction, carboxyl groups, in this case, from the PMAA hydrogel, are activated to an o-Acylisourea ester intermediate using EDC. Next, NHS converts the ester intermediate to an amine-reactive NHS ester. When a primary amine is present, such as the N-terminus or lysine sidechains within a protein, the amine will react with the NHS ester, forming a peptide bond. Hydrogels were cut into either 1.0 or 1.5 $cm^2$ coupons prior to use and placed into individual wells of either 48- or 24-well plates. The hydrogel surfaces were cleaned with copious amounts of water prior to use. To perform the EDC-NHS coupling, 0.4 M EDC and 0.1 M NHS were prepared fresh and dissolved in water. Immediately prior to use, EDC and NHS were mixed 1:1, and only used for a single activation round. Enzyme was then added to 1 µM final concentration for dPTE2 and 1 mg/ml for β-lactamase, and the EDC-NHS-enzyme mixture was immediately added to each hydrogel coupon, sufficient to cover the hydrogel surface. Hydrogels were incubated with this mixture with shaking at 120 rpm. Hydrogels were cut to create ~1 $cm^2$ coupons containing dPTE2 and 0.36 $cm^2$ coupons containing β-lactamase. Embodiments of the present invention encompass the use of other concentrations, solvents, times, rotations, and sizes.

Various incubation procedures were investigated. In some instances, it was found that enzyme and hydrogel, for example a $(PMAA)_{20}$ hydrogel, could be incubated under certain conditions to achieve a desired level of loading of the enzymes into the hydrogel framework. In some instances, the enzyme dPTE2 was selected. The enzyme dPTE2 is a designed mutant of bacterial phosphotriesterase exhibiting high expression and stability that is also of biotechnological potential for reaction, decontamination, and detoxification of organophosphates. Fluorescently-labeled dPTE2 was used to investigate the loading process, with the understanding that a greater fluorescence intensity of the hydrogel likely corresponds to the amount of enzyme loaded. The fluorescently-labeled dPTE2 was incubated along with a mixture of EDC-NHS and the $(PMAA)_{20}$ hydrogel in a well plate and shaken. Fluorescence microscopy images were measured for their fluorescent intensity, and the normalized intensities plotted as a function of time. The results are depicted in FIG. 3.

Figure 3:
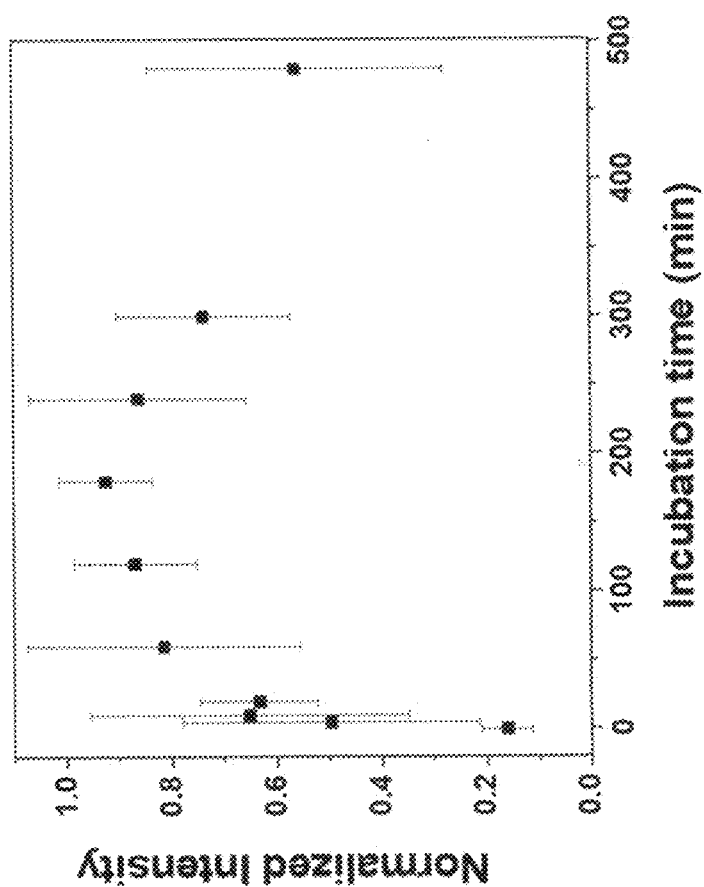
FIG. 3 illustrates aspects of a hydrogel-enzyme fabrication process according to certain embodiments of the invention.

FIG. 3 depicts the results of loading of dPTE2 into $(PMAA)_{20}$ hydrogel. Fluorescence intensity measurements of fluorescently-labeled dPTE2 loaded into hydrogels at different times were recorded. The intensity was normalized to the maximum fluorescence observed for a particular hydrogel. The error bars represent standard deviation of three independent experiments (n=3). It was observed that a rapid increase in the fluorescence intensity occurred within approximately 15 minutes of the start of the incubation. Within 60 minutes to 180 minutes, there was a leveling-off of the measured fluorescent intensity, which, upon further incubation time led to a decrease in the overall fluorescence intensity until 480 minutes. Without being bound by any particular theory, it is believed that this decrease in fluorescence intensity is possibly a result of photobleaching or the fluorescent enzyme reaching a true equilibrium between hydrogel and solution. Nevertheless, based on the data, it can be determined that according to some embodiments, approximately 120 minutes can be a sufficient time for loading of enzymes into the hydrogels.

In exemplary experiments, fluorescently-labeled protein was used to determine desired or target loading times. Alexa Fluor 488 $C_5$ maleimide dye was used to fluorescently-label dPTE2, via the reaction on the maleimide moiety with protein thiol groups. As described elsewhere herein for the incorporation of enzyme into hydrogels, the incubation of hydrogel with the EDC-NHS-enzyme mixture using fluorescently-labeled dPTE2 was performed, but for various timepoints, at which point the mixture was removed and the hydrogel surface vigorously washed with water. These washed hydrogels were then imaged. Imaging of the hydrogel surfaces was performed in an inverted confocal fluorescence microscope using imaging software. For each hydrogel, at least three regions of 830 µm×830 µm were imaged, and their total fluorescence intensity measured. This was repeated with three, independent hydrogel coupons for each timepoint (n=3). Intensities for a particular timepoint were normalized against the highest average intensity for a particular independent experiment, and the normalized intensities averaged across all three experiments.

Without being bound by any particular theory, it is believed that in some embodiments, enzymes may be present inside the hydrogel structure. Relatedly, without being bound by any particular theory, it is believed that in some embodiments, enzymes may only interact with the surface of the hydrogel. Further, without being bound by any particular theory, it is believed that in some embodiments, enzymes may be present inside the hydrogel structure and may also interact with the surface of the hydrogel. Without being bound by any particular theory, it is believed that the hydrogel mesh size can be tailored to beneficially incorporate or exclude a particular enzymatic volume, and/or that mesh size can be manipulated, designed, or selected for desired performance. A cross-link density of a PMAA hydrogel was calculated. Specifically, $(PMAA)_{20}$ dry hydrogel films exposed to a 10 mM phosphate buffer at pH 4.6 resulted in an increase in film thickness from 53.1 nm to 137.7 nm measured by in-situ ellipsometry. Since ionic forces have no effect on the increase of thickness due to the fact that PMAA does not carry an electric charge at pH 4.6, a Flory equation for nonionic gels was used to calculate mesh size of the $(PMAA)_{20}$ hydrogel. Using the hydrogel swelling data measured by in situ ellipsometry, the mesh size of the hydrogel at this condition was calculated to be 7.1 nm. The analyses of mesh size of the hydrogel, molecular weight and radius of gyration of enzymes, MW of ~30 kDa for δ-lactamase and 80 kDa for dPTE2, and Rg between 1.7-2.0 nm for β-lactamases and 2.8-4.5 nm for dPTE2, indicate that enzymes have the potential to diffuse into and throughout the hydrogel.

It was also investigated whether hydrogel-bound enzymes possessed their native activities (e.g., following loading of the enzymes into the hydrogels). Paraoxon, an organophosphate oxon, and the active metabolite of the insecticide parathion is a known substrate for dPTE2. The paraoxon reaction activity of dPTE2-bound hydrogels in the presence of 100 µM paraoxon was investigated using UV-Vis spectroscopy. The reaction on paraoxon with dPTE2 forms para-nitrophenol, which possesses a distinct $\lambda_{max} \approx 405$ nm in slightly basic solution and allows for simple tracking of the reaction progress even by eye, as the solution turns yellow during the reaction. Activity within the hydrogel for dPTE2 towards paraoxon reaction was found.

Figure 4A:
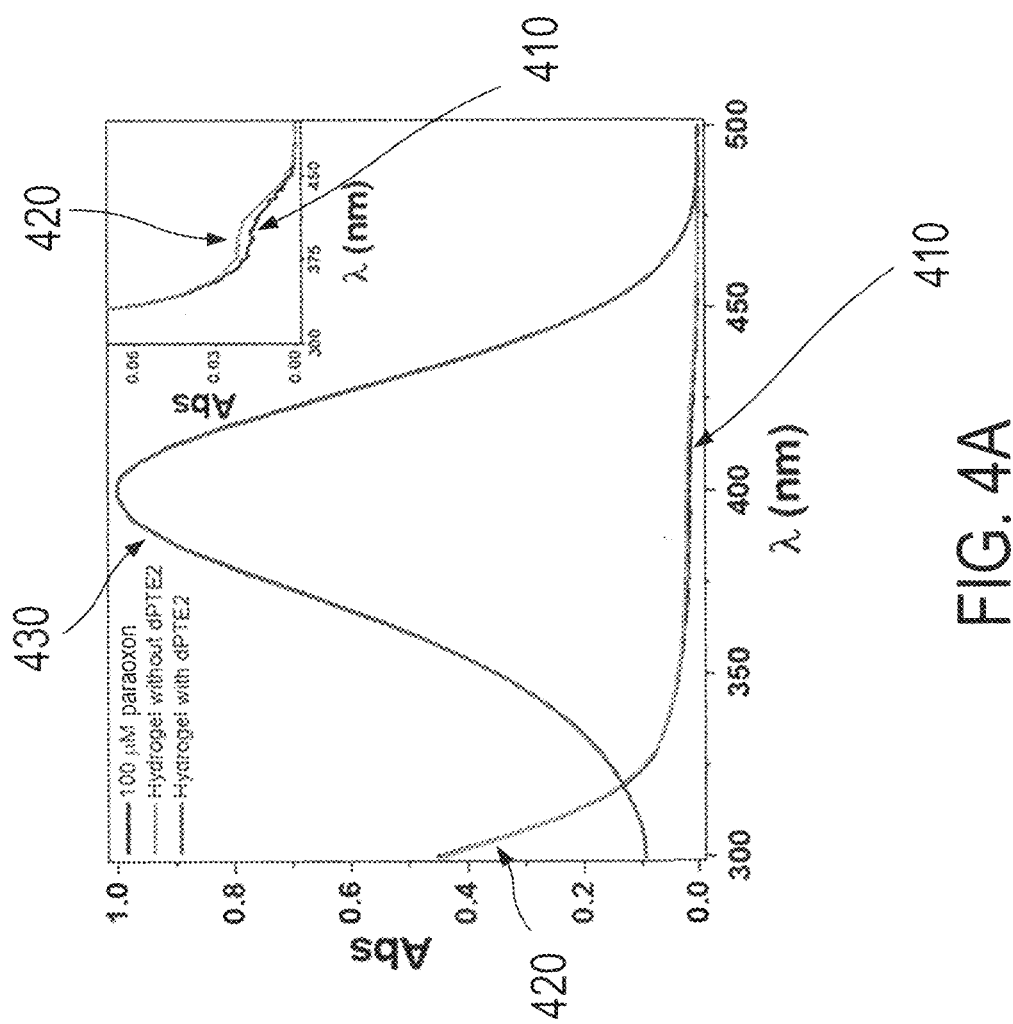
FIG. 4A illustrates performance aspects of a hydrogel-enzyme system according to certain embodiments of the invention.

In hydrogels without dPTE2, paraoxon reaction activity was not observed, whereas in hydrogels containing bound dPTE2, a characteristic peak is observed, indicating the formation of the product, para-nitrophenol, as shown in FIG. 4A. Curve 410 represents the absorbance of a 100 µM paraoxon solution. Curve 420 represents results with hydrogel without dPTE2. Curve 430 represents results with hydrogel with dPTE2. These results suggested that the hydrogels are capable of incorporating an active form of dPTE2. FIG. 4A depicts the reactivity of protein-loaded hydrogel in 100 mM Tris pH 8, 100 mM NaCl, and 100 µM $ZnCl_2$. Ultraviolet-visible absorbance measurements of reactant (paraoxon, line 410), paraoxon after being exposed to the $(PMAA)_{20}$ hydrogel without dPTE2 (line 420), and paraoxon after being exposed to the $(PMAA)_{20}$ hydrogel with dPTE2 (line 430) are shown. Product formation of the reaction on paraoxon to para-nitrophenol is observed only in the case where dPTE2 is coupled within the hydrogel. The inset shows a zoomed-in view of the λmax region of para-nitrophenol absorbance for lines 410 and 420.

In exemplary experiments, a temperature denaturation determination of hydrogel-bound and solution dPTE2 was performed. The same procedure for the paraoxon reaction activity assay was used as described elsewhere herein, with modifications. After an initial assay, the coupon was placed on a glass slide and into an oven at the specified temperature and heated for 30 minutes. After heating, the glass slide and hydrogel coupon were removed and kept at 25° C. for 20 minutes to cool. The paraoxon reaction activity assay was then repeated on the heat treated coupon. For each data point corresponding to a specific temperature, duplicate, independent assays using different hydrogel coupons were carried out (n=2). Residual activity was determined by comparing the slope of the $\Delta Abs_{405nm}$ for the assay pre- and post-heat treatment. For solution studies, a similar procedure was performed, except 1 mL of buffer-protein solution, containing 1 µM dPTE2, was kept in a sealed vial during heating to minimize evaporation.

It was also investigated whether the hydrogel possessed the ability to provide improved stability of the enzyme towards challenges, such as temperature. The effect that increased temperature would have on the activity of dPTE2 both in solution and in the hydrogel was examined. It has been reported that the inactivation temperature of dPTE2 in solution is 62° C. The activity of individual dPTE2-bound hydrogel coupons at room temperature was measured, the hydrogel coupons were heated at a specific temperature for 30 minutes, then the activity was measured again after 20 minutes to allow the hydrogel coupons to cool to room temperature. Without being bound by any particular theory, it is believed that the hydrogel may operate to prevent the enzyme from unfolding and/or denaturing under the higher temperature conditions.

Figure 4B:
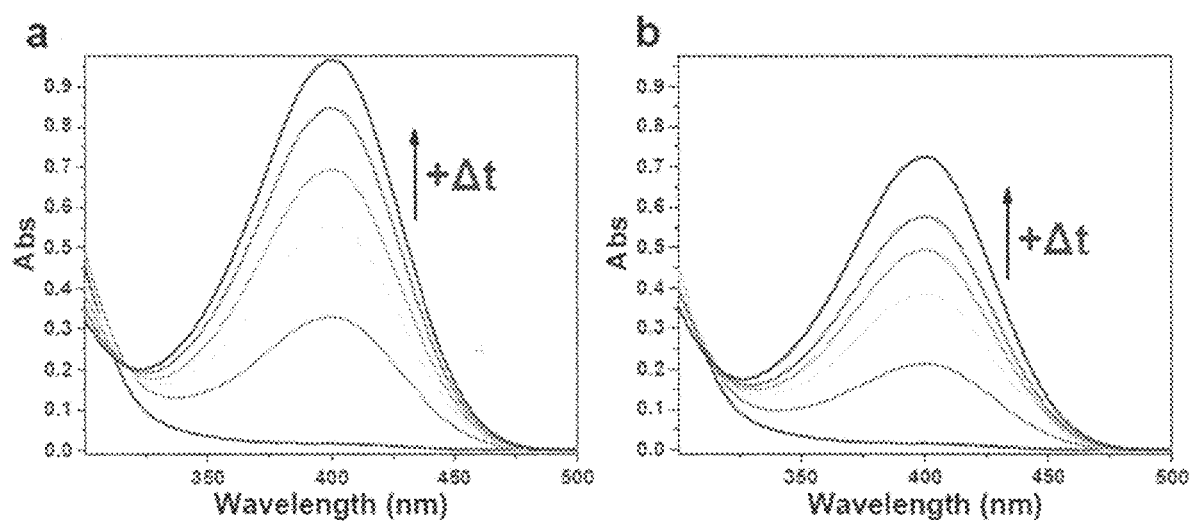
FIG. 4B illustrates performance aspects of a hydrogel-enzyme system according to certain embodiments of the invention.

FIG. 4B depicts representative UV-Vis absorbance time-course measurements of dPTE2-loaded hydrogel reacting with 100 µM paraoxon (left panel) at 25° C., and then (right panel) at 25° C. after 30 minutes incubation at 220° C. Arrows indicate the direction of change of the spectra with increasing time. Activity is observed in both assays, suggesting a catalytically active protein-based species is present in both hydrogels.

Figure 5A:
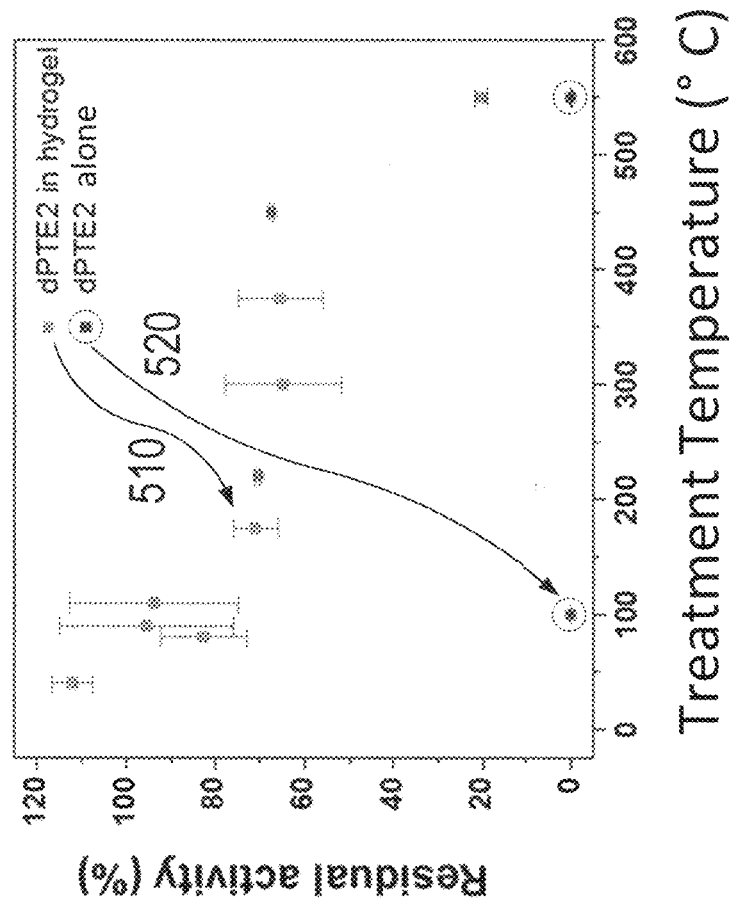
FIG. 5A illustrates performance aspects of a hydrogel-enzyme system according to certain embodiments of the invention.

In some embodiments, the hydrogel can be heated at temperatures up to for example 550° C. for 30 minutes, and then the hydrogel can be allowed to cool at room temperature for 20 minutes. Initially, with no heating (i.e., keeping the hydrogel at room temperature, but only rinsing and replacing the buffer solution and substrate), a similar activity for both assay rounds was observed, as depicted in FIG. 5A. The high temperature condition is between about 40° C. and about 450° C. (i.e., within a few degrees) and the residual activity is between about 64% and about 100% (i.e., within a few percentages). The increase above 100% activity can be attributed to slight experimental variations. Exposure to extremely high temperature treatment conditions were investigated, and the assays are done at 25° C. (room temperature). The results here show a remarkable and unexpectedly surprising increase in the thermostability of the hydrogel-bound dPTE2 compared to dPTE2 alone towards paraoxon reaction. With reference to the term "dPTE2 alone," it is meant that the material is all dried out, and there is no solution, when it is subjected to 500° C. for 30 minutes, according to some embodiments. FIG. 5A depicts the reactivity of dPTE2-loaded hydrogel and dPTE2 alone after 30 minutes incubation at various temperatures. Residual activity of paraoxon reaction activity of dPTE2 in hydrogel (squares 510), and dPTE2 alone (squares 520) is shown. Activity measurements were taken in 100 mM Tris pH 8.0, 100 mM NaCl, and 100 µM $ZnCl_2$. A more robust activity against temperature inactivation of enzymes loaded into hydrogels compared to enzymes alone is observed. Error bars represent the standard deviation of duplicate experiments (n=2).

Indeed, dPTE2 within the hydrogel network was observed to maintain residual activities of >60% after heating at 450° C. Even heating at 550° C., a residual activity of approximately 20% remains. Without being bound by any particular theory, it is believed that encapsulation within the hydrogel layers and confinement within the hydrogel pores created by the crosslinker molecule EDA may be responsible for the increased temperature stability of the enzyme within the hydrogel as compared to enzyme alone. This level of thermostability observed was unexpected, and the impact of the hydrogel on the performance of the enzyme embedded therein under such high temperatures was unexpected. It may also be possible that the hydrogel operates to confer some amount of enhanced thermostability to the enzyme, and/or some amount of thermal denaturation protection to the enzyme.

Figure 5B:
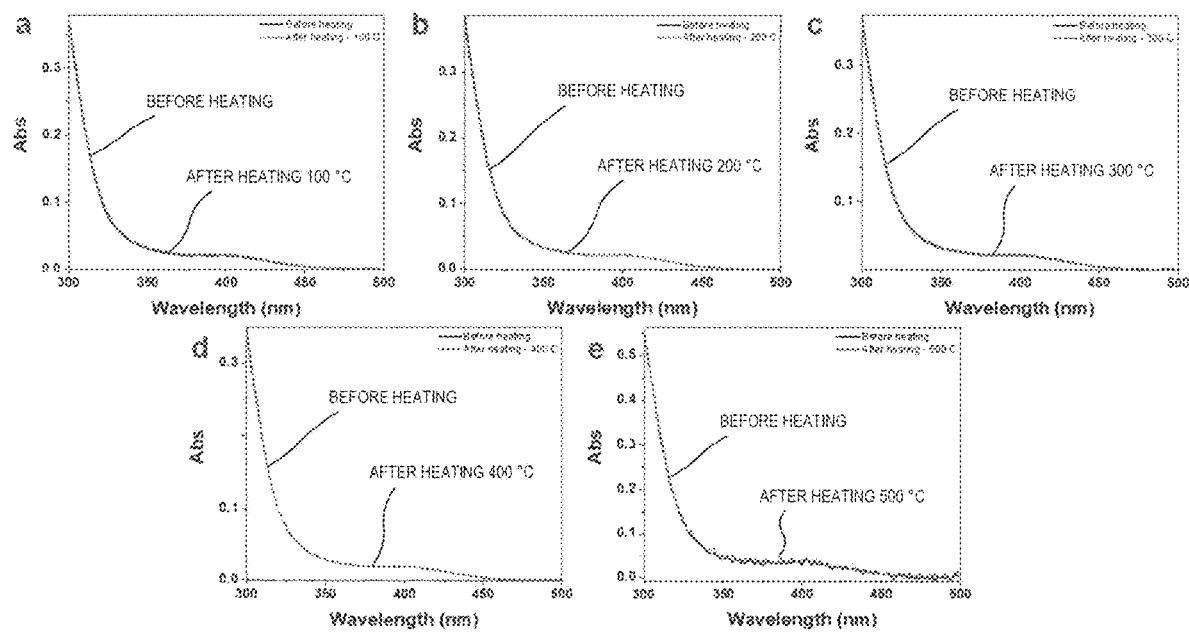
FIG. 5B illustrates performance aspects of a hydrogel system according to certain embodiments of the invention.

In order to rule out the possibility of a catalytically active species in the hydrogel being formed during high heating, the experiment was repeated with a hydrogel without enzyme (unloaded). FIG. 5B depicts representative UV-Vis absorbance measurements of unloaded hydrogels reacted with paraoxon at 25° C., and then after 30 minutes incubation at (a) 100, (b) 200, (c) 300, (d) 400, and (e) 500° C. Solution absorbance measurements before heating and after heating were taken in 100 mM Tris pH 8.0, 100 mM NaCl, and 100 µM $ZnCl_2$ buffer with 100 µM paraoxon after a 45 min incubation. No paraoxon reaction is observed in any case, suggesting a catalytically active hydrogel-based species is not formed during the heating process and is not the cause of paraoxon reaction observed in FIG. 5A.

Figure 5C:
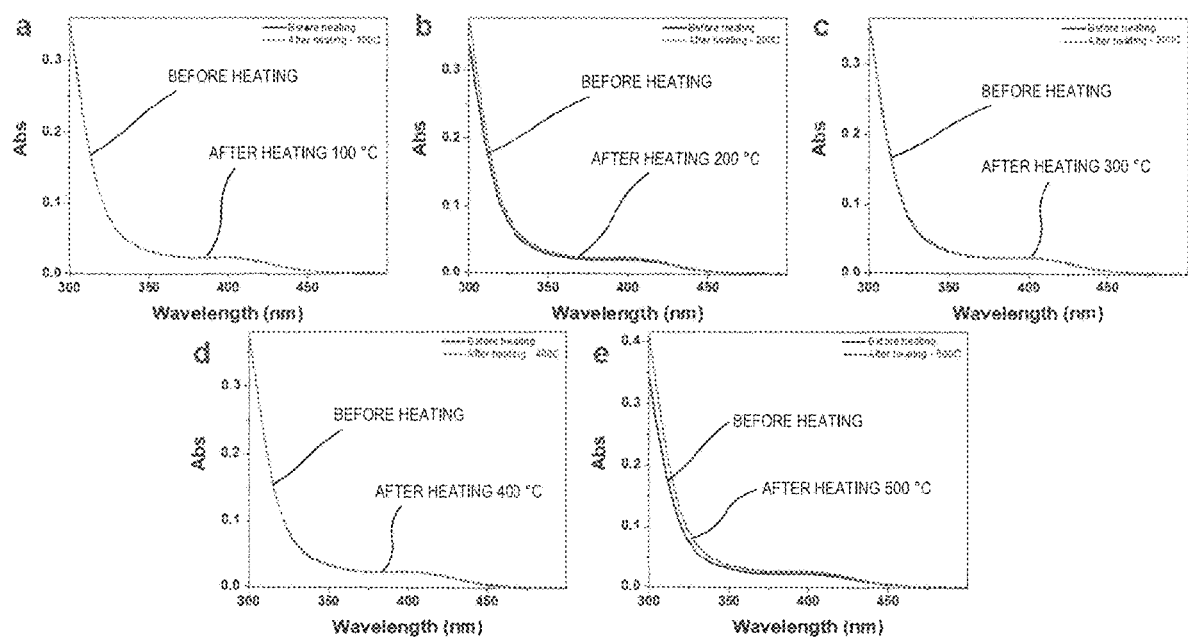
FIG. 5C illustrates performance aspects of a hydrogel-enzyme system according to certain embodiments of the invention.

Additionally, in order to rule out the possibility of a protein-based catalytically active species being formed during high heating, the experiment was repeated with a Bovine Serum Albumin (BSA)-loaded hydrogel. FIG. 5C depicts representative UV-Vis absorbance measurements of BSA-loaded hydrogels reacted with paraoxon at 25° C., and then after 30 minutes incubation at (a) 100, (b) 200, (c) 300, (d) 400, and (e) 500° C. Solution absorbance measurements before heating and after heating were taken in 100 mM Tris pH 8.0, 100 mM NaCl, 100 µM $ZnCl_2$ buffer with 100 µM paraoxon after a 45-minute incubation. No paraoxon reaction is observed in either case, suggesting a new catalytically active protein-based species is not formed during the heating process. Both of these cases suggest that the active species within the dPTE2-loaded hydrogel is dPTE2 itself, and that it is capable of maintaining its activity despite being subjected to extreme heat and desiccation.

Based on the observations with dPTE2-loaded hydrogels, it was also investigated whether the improved thermostability of enzymes within the hydrogel network was present in other instances. β-lactamase was selected as another enzyme for testing in hydrogels. β-lactamases are a broad class of enzymes that catalyze the hydrolysis of β-lactam antibiotics, leading to drug resistance in Gram-negative bacteria. β-lactamase was selected at least in part based on its rapid rate of reaction, absorbance-based activity measurements with substrates such as nitrocefin, low cost, and commercial availability. Reactions with nitrocefin can be monitored by loss of nitrocefin absorbance at 380 nm and an increase in a by-product absorbance at 500 nm.

Figure 6A:
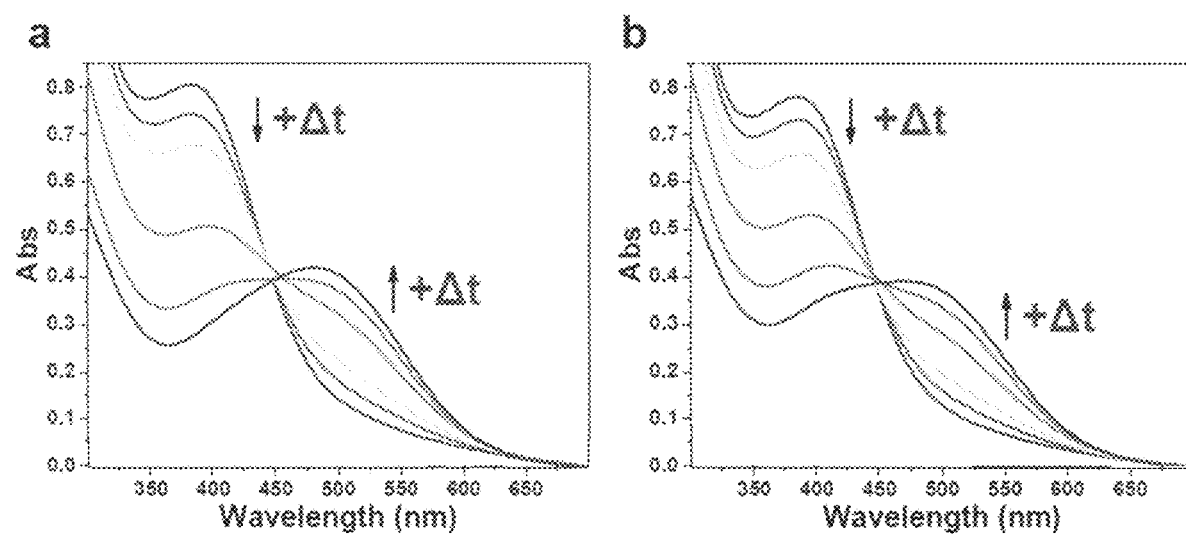
FIG. 6A illustrates performance aspects of a hydrogel-enzyme system according to certain embodiments of the invention.

FIG. 6A depicts representative UV-Vis absorbance time-course measurements of solutions with β-lactamase-loaded hydrogel reacting with nitrocefin (a) at 25° C., and then (b) at 25° C. after 30 minutes incubation at 400° C. Arrows indicate the direction of change of the spectra with increasing time. Activity is observed in both cases, suggesting a catalytically active protein-based species is present.

Figure 6B:
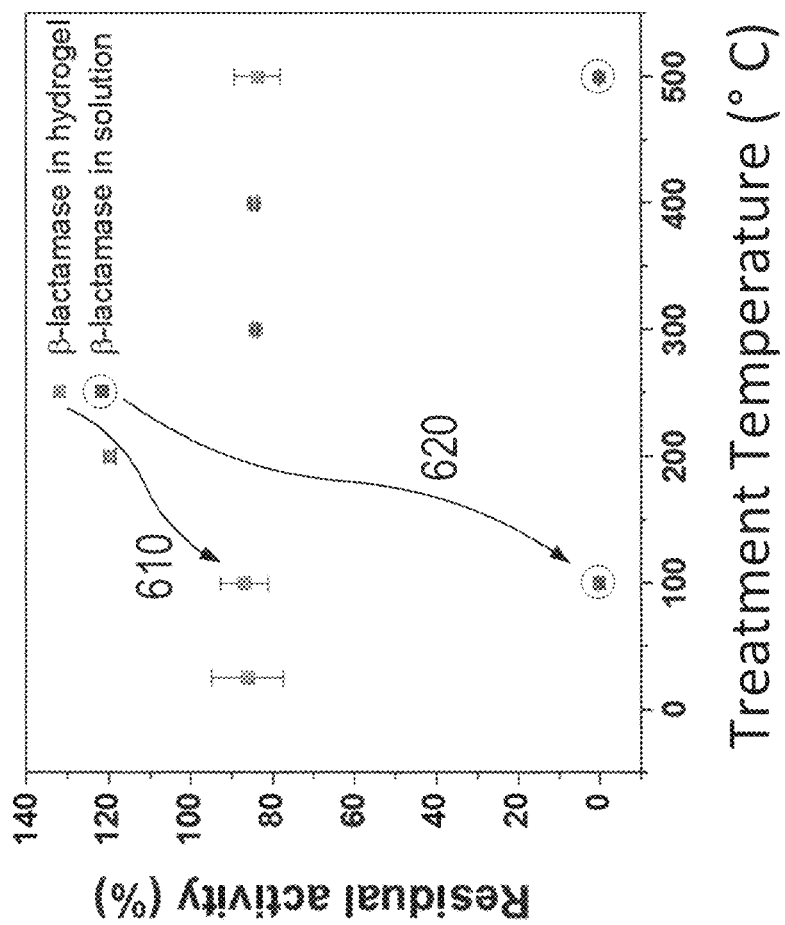
FIG. 6B illustrates performance aspects of a hydrogel-enzyme system according to certain embodiments of the invention.

The activity of individual β-lactamase-bound hydrogels was measured at room temperature. The hydrogel was heated at a specific temperature for 30 minutes, then the hydrogel was allowed to cool back to room temperature for 20 minutes before measuring the activity again. Again, an extreme level of thermostability for β-lactamase within the hydrogel was observed, as depicted in FIG. 6B. In fact, no appreciable decrease was observed in residual activity even after heating to temperatures as high as 500° C., with all measurements >80% residual activity.

FIG. 6B illustrates the reactivity of β-lactamase hydrogel and β-lactamase in solution after 30 minutes incubation at various temperatures. Nitrocefin is a chromogenic cephalosporin substrate that can be used to detect the presence of β-lactamase enzymatic activity. The residual activity of nitrocefin reaction activity of β-lactamase in hydrogel (610), and in solution (620) is shown. Activities were taken in PBS. Error bars represent the standard deviation of duplicate experiments (n=2).

This evidence reinforces the finding that the $(PMAA)_{20}$ hydrogels help to confer thermostability to bound enzymes, and, furthermore, that this effect is not limited to a particular enzyme, but is applicable for other enzymes in general. As in the case of dPTE2, the experiments with unloaded and BSA-loaded hydrogels were repeated.

Figure 6C:
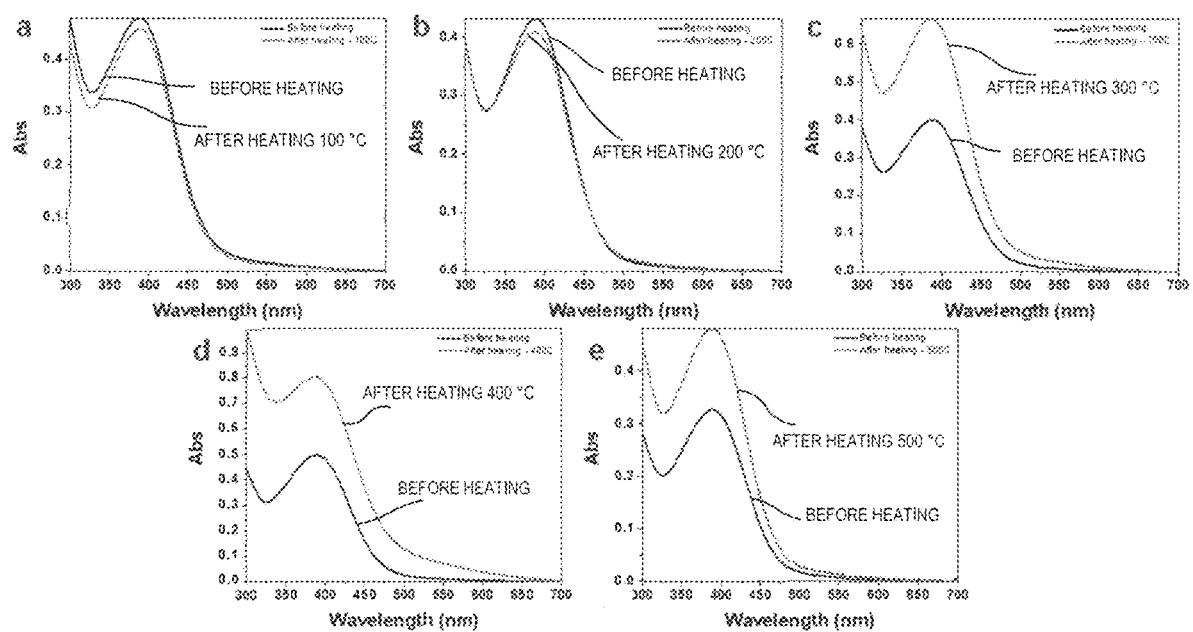
FIG. 6C illustrates performance aspects of a hydrogel system according to certain embodiments of the invention.

FIG. 6C depicts representative UV-Vis absorbance measurements of unloaded hydrogel reacted with nitrocefin at 25° C., and then after 30 m incubation at (a) 100, (b) 200, (c) 300, (d) 400, and (e) 500° C. Absorbance measurements before heating and after heating were taken in PBS with 50 µM nitrocefin after a 45 min incubation. No activity towards nitrocefin reaction is observed in any case, as no by-product is formed, as evidenced by the lack of absorbance at 480-500 nm, suggesting a catalytically active hydrogel-based species is not formed during the heating process.

Aside from baseline shifts due to solubility issues of nitrocefin in PBS, no nitrocefin reaction activity of the unloaded or BSA-loaded hydrogels before or after heating was observed. These results indicate that δ-lactamase itself is responsible for the activity we observed.

In exemplary experiments, a temperature denaturation determination of hydrogel-bound and solution δ-lactamase was performed. Recombinant δ-lactamase was used, along with ~0.36 $cm^2$ hydrogel coupons, in a 48-well plate to perform the assay. Freshly prepared solutions of 50 µM nitrocefin in phosphate-buffered saline (PBS) were used as substrate for each assay. Experiments were performed in low light due to the light sensitivity of the substrate. 300 µL of the substrate solution was added to one well containing a single coupon. The plate was shaken at 180 rpm throughout the course of the assay. Activity measurements were performed by taking 100 µL of the well solution and measuring the UV-Vis absorbance of the product, hydrolyzed nitrocefin ($\lambda_{max} \approx 500$ nm), and then returning the aliquot back to the well. Between each measurement, the UV-Vis cuvette was thoroughly rinsed and dried using a vacuum-driven cuvette washer. The assay was carried out for 45 minutes. Heating was performed as described elsewhere herein. The assay was then repeated on the heat-treated coupon. For each data point corresponding to a specific temperature, duplicate, independent assay using different hydrogel coupons were carried out (n=2). Residual activity was determined by comparing the slope of the $\Delta Abs_{500nm}$ for the assay pre- and post-heat treatment.

As an alternative to using multilayer PMAA hydrogels, embodiments of the present invention encompass the use of other types of hydrogels with enzymes embedded therein. As an alternative to using EDC/NHS linking chemistry to couple enzymes to hydrogels, it is possible to use other types of carboxyl-amine covalent linking chemistries. Additional aspects of suitable linking chemistries are discussed in Podual et al. "*Preparation and dynamic response of cationic copolymer hydrogels containing glucose oxidase*," Polymer 41 (11), 3975-3983 (2000) and Campbell et al. "*Hydrogel—Immobilized Supercharged Proteins*," Advanced Biosystems 2 (7), 1700240 (2018), the contents of each of which are incorporated herein by reference. Relatedly, exemplary preparation techniques include chemistries which are operable to link carboxyls with amine groups.

Figure 7:
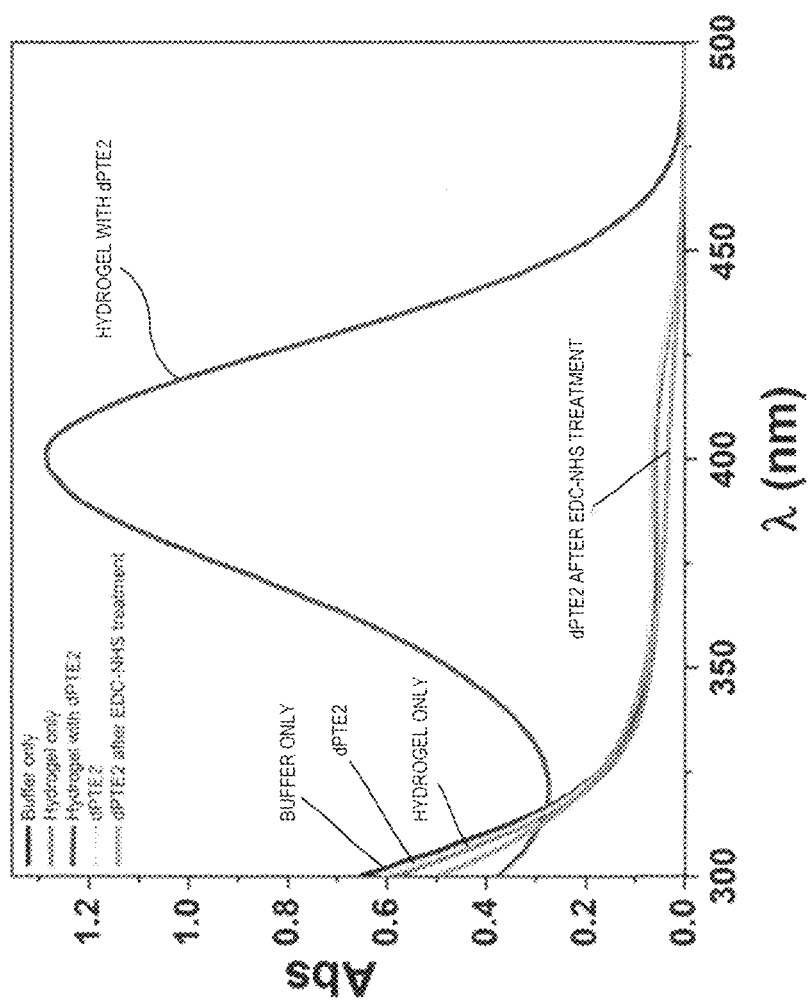
FIG. 7 illustrates performance aspects of a hydrogel-enzyme system according to certain embodiments of the invention.

FIG. 7 illustrates representative UV-Vis absorbance measurements of various sample solutions after 30 minutes of exposure to 100 µM paraoxon at 90° C. The buffer used was 100 mM Tris pH 8.0, 100 mM NaCl, and 100 µM $ZnCl_2$. Measurements were taken of buffer only, $(PMAA)_{20}$ hydrogel without dPTE2, $(PMAA)_{20}$ hydrogel with dPTE2, dPTE2 in buffer, and dPTE2 in buffer after EDC-NHS treatment. Significant paraoxon reaction activity, as observed from the ~400 nm peak, is observed only in the case of hydrogel-bound dPTE2, indicating that activity remains even in a high temperature environment (e.g., 90° C. or higher approaching 100° C.), well above the reported inactivation temperature of dPTE2. It has been reported that the inactivation temperature of dPTE2 in solution is 62° C., and hence the performance of the hydrogel-enzyme construct at 90° C. provides a surprisingly unexpected result. Without being bound by any particular theory, it is believed that the hydrogel may operate to prevent the enzyme from unfolding and/or denaturing under the higher temperature conditions. Thus, the operational high temperature bound of the enzyme can be extended when embedded in the hydrogel. It is understood that the temperature 90° C. was selected as a high temperature below 100° C. in this example, but that a different high temperature approaching 100° C. (e.g., 99° C. or higher but below 100° C.) may be used to demonstrate the performance of the hydrogel-enzyme construct.

Embodiments of the present invention encompass the use of hydrogels as layered polymeric structures, where enzymes are embedded into the hydrogel structure, for example via covalent bonding. In exemplary embodiments, an enzyme that is embedded in the hydrogel can be selected based on its functionality, for example its ability to react (build upon or degrade) a particular chemical substrate. It is believed that the hydrogel may operate to protect the enzyme from being degraded or denatured in extremely high temperature environments. Embodiments of the present invention encompass the hydrogel-enzyme compositions or structures themselves, as well as methods of manufacturing and using such hydrogel-enzyme compositions or structures, for example to perform catalytic functions in extremely high temperature environments. In particular embodiments, the hydrogel can be a PMAA hydrogel and the enzyme can be an enzyme that builds upon or degrades organophosphate(s), such as dPTE2. It has unexpectedly been discovered that the hydrogel with the embedded enzyme can withstand temperatures up to 500° C. and still retain the functionality of the embedded enzyme to react with the organophosphate(s). Embodiments encompass the use of a variety of other hydrogels and/or enzymes. Hydrogel-enzyme constructs can be subjected to extremely high temperatures and desiccation conditions and still retain their catalytic activity after cooling, thereafter operating in the enzyme's normal operational range.

According to some embodiments, hydrogel-enzyme constructs confer the ability to increase the operational range of an enzyme. A hydrogel-enzyme construct can have catalytic activity outside the reported operational range of the enzyme. The hydrogel-enzyme construct can extend and expand the operational range of the enzyme. For example, whereas dPTE2 loses activity at 62° C. when free in solution, it retains its activity up to 90° C. (see, e.g., FIG. 7) when embedded in the hydrogel. In some cases, a hydrogel-enzyme construct is capable of performing enzymatic reaction on a reactant when the reactant is exposed to the hydrogel-enzyme construct under a temperature condition of up to 90° C. or a higher temperature approaching 100° C. (e.g., 99° C. or higher but below 100° C.).

According to some embodiments, hydrogels are composed of aqueous swellable, crosslinked polymer networks consisting of a variety of natural or synthetic components. Exemplary hydrogels may exhibit a stabilizing effect on the catalytic function of enzymes embedded therein, in extremely high temperature conditions. In some embodiments, hydrogel-enzyme constructs may exhibit extremely high temperature tolerances with regard to the catalytic activity of the enzymes embedded in the hydrogels.

As discussed elsewhere herein, exemplary hydrogel-enzyme constructs can retain catalytic activity following exposure to very high temperature and/or very low moisture conditions. Relatedly, hydrogel-enzyme constructs can perform catalytic activity not only above their normal temperature bound, but also following extensive heating and desiccation. In some cases, a hydrogel-enzyme construct can become desiccated when exposed to high temperatures, such as 550° C. In some cases, a hydrogel-enzyme construct can become desiccated when exposed to low moisture environments. Exemplary hydrogel-enzyme constructs can be desiccated using high heat and/or low moisture conditions, and then rehydrated to at least partially restore catalytic activity. In some cases, the rehydration can be achieved by placing the desiccated hydrogel-construct in an aqueous solution. In some cases, the rehydration can be achieved by placing the desiccated hydrogel-enzyme construct in air, whereby ambient moisture in the air can operate to at least partially rehydrate the construct. Without being bound by any particular theory, it is believed that the enzyme in the hydrogel-enzyme construct can retain its conformational structure in low moisture environments (e.g., in air) and catalytic activity of the enzyme can be present in the vapor phase.

Figure 8:
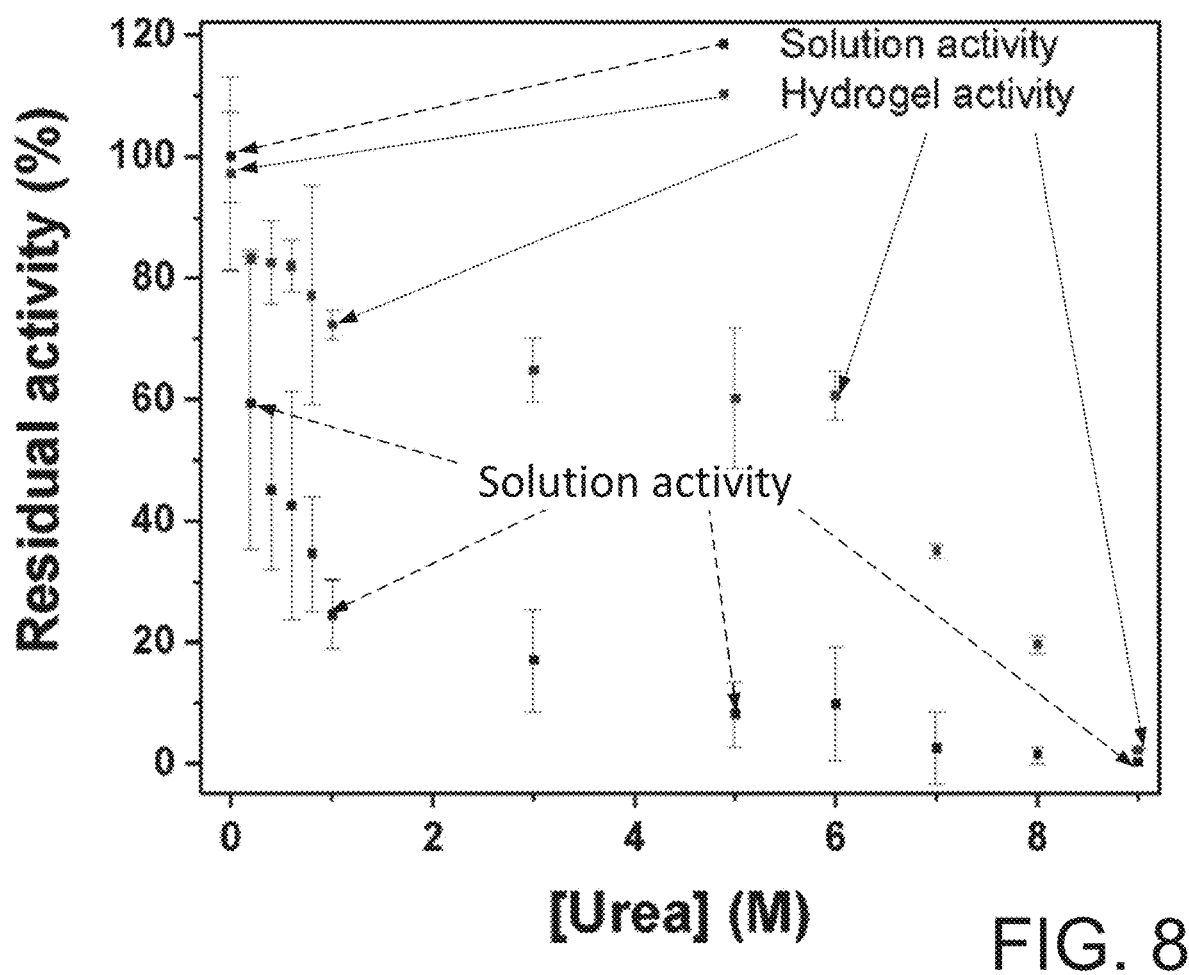
FIG. 8 illustrates performance aspects of a hydrogel as a chemo-protectant for enzymes which is resistant to urea as an example of a chemical denaturant.

Urea is known to behave as a chemical denaturant by binding to enzymes, interfering with the folding mechanism of the active state, and causing unfolding of enzymes to render them inactive. FIG. 8 illustrates representative activity data in the presence of an added concentration of urea for dPTE2 free in solution versus embedded in a hydrogel. Degradation of paraoxon by dPTE2 is the metric for Residual activity. As noted in the figure, only 0.5M urea is sufficient to notably reduce the activity of free dPTE2 in solution down to 60%. Higher concentrations of urea (>1M) quickly lower the dPTE2 activity to below 20% of its initial activity when the enzyme is free in solution. In contrast to this, when dPTE2 is embedded within the protective environment of the hydrogel, it takes 8M urea to drop its activity to 20% of the initial activity. This evidence supports the finding that the hydrogel acts as a chemo-protectant environment to prevent chemical denaturation of the embedded enzymes. Without being bound by any particular theory, it is believed that the enzyme in the hydrogel-enzyme construct can retain its conformational structure in the presence of chemical denaturants that otherwise initiate unfolding in solution.

As will be appreciated by one of ordinary skill in the art, the present invention may be embodied as an apparatus (including, for example, a system, a machine, a device, and/or the like), as a method (including, for example, a business process, and/or the like), or as any combination of the foregoing.

Embodiments of the invention can be manifest in the form of methods and apparatuses for practicing those methods.

Unless explicitly stated otherwise, each numerical value and range should be interpreted as being approximate as if the word "about" or "approximately" preceded the value or range.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

All documents mentioned herein are hereby incorporated by reference in their entirety or alternatively to provide the disclosure for which they were specifically relied upon.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. A method of performing high temperature enzymatic reaction on an organophosphate reactant, the method comprising:

providing a hydrogel-enzyme construct, the construct comprising a hydrogel having multiple layers of a poly(methacrylic acid) (PMAA) hydrogel polymer and a plurality of phosphotriesterase molecules, wherein adjacent hydrogel polymer layers are connected via crosslinking, individual phosphotriesterase molecules are embedded between adjacent hydrogel polymer layers, and individual phosphotriesterase molecules are covalently bonded with respective individual hydrogel polymer layers;

exposing the hydrogel-enzyme construct to a high temperature condition of up to 550° C.; and exposing the organophosphate reactant to the hydrogel-enzyme construct following the high temperature exposure step, wherein enzymatic reaction on the organophosphate reactant by individual phosphotriesterase molecules embedded within the hydrogel occurs at a residual activity of between 20% and 100%, wherein the plurality of phosphotriesterase molecules comprise Protein Repair One Stop Shop (PROSS) stabilized PTE S5 from *Pseudomonas diminuta* S5 variant (dPTE2), and the organophosphate reactant is paraoxon.

2. The method according to claim 1, wherein the adjacent hydrogel polymer layers are connected via ethylenediamine cross-linking.

3. The method according to claim 1, wherein the enzymatic reaction on the organophosphate reactant by individual phosphotriesterase molecules embedded within the hydrogel occurs at a residual activity of between 20% and 100% following or together with exposure to a chemical denaturant in a concentration that reduces a residual activity to below 20% in a solution containing free phosphotriesterase molecules.

4. A hydrogel-enzyme construct for performing high temperature enzymatic reaction on an organophosphate reactant, the hydrogel-enzyme construct comprising:
a hydrogel having multiple layers of a poly(methacrylic acid) (PMAA) hydrogel-polymer; and
a plurality of phosphotriesterase molecules,
wherein adjacent hydrogel polymer layers are connected via cross-linking, individual phosphotriesterase molecules are embedded between adjacent hydrogel polymer layers, individual phosphotriesterase molecules are covalently bonded with respective individual hydrogel polymer layers, and the hydrogel-enzyme construct is capable of performing enzymatic reaction on the organophosphate reactant after the hydrogel-enzyme construct is exposed to a high temperature condition of up to 550° C., the enzymatic reaction on the organophosphate reactant by individual phosphotriesterase molecules embedded within the hydrogel occurring at a residual activity of between 20% and 100%,
wherein the plurality of phosphotriesterase molecules comprise Protein Repair One Stop Shop PROSS) stabilized PTE S5 from *Pseudomonas diminuta* S5 variant (dPTE2), and the organophosphate reactant is paraoxon.

5. The hydrogel-enzyme construct according to claim 4, wherein the adjacent hydrogel polymer layers are connected via ethylenediamine cross-linking.

6. The hydrogel-enzyme construct according to claim 4, wherein the hydrogel-enzyme construct is capable of performing enzymatic reaction on the organophosphate reactant when the hydrogel-enzyme construct is exposed to a chemical denaturant, the enzymatic reaction on the organophosphate reactant by individual phosphotriesterase molecules embedded within the hydrogel occurring at a residual activity of between 20% and 100% following or together with exposure to a chemical denaturant in a concentration that reduces a residual activity to below 20% in a solution containing free phosphotriesterase molecules.

7. A method of performing high temperature enzymatic reaction on an organophosphate reactant, the method comprising:
providing the hydrogel-enzyme construct according to claim 4; and
exposing the organophosphate reactant to the hydrogel-enzyme construct at a temperature condition of up to above 99° C. and below 100° C.

8. The hydrogel-enzyme construct according to claim 4, wherein the hydrogel-enzyme construct is capable of performing enzymatic reaction on the organophosphate reactant when the organophosphate reactant is exposed to the hydrogel-enzyme construct under a temperature condition of up to above 99° C. and below 100° C.

9. The method according to claim 1, wherein the dPTE2 is obtained from Addgene plasmid #111634 (SEQ ID NO: 1).

10. The hydrogel-enzyme construct according to claim 4, wherein the dPTE2 is obtained from Addgene plasmid #111634 (SEQ ID NO: 1).

11. The method according to claim 1, comprising exposing the hydrogel-enzyme construct to a high temperature condition in a range between 40° C. and 450° C., wherein enzymatic reaction on the organophosphate reactant by individual phosphotriesterase molecules embedded within the hydrogel occurs at a residual activity of between about 64% and 100%.

12. The hydrogel-enzyme construct according to claim 4, wherein the hydrogel-enzyme construct is capable of performing enzymatic reaction on the organophosphate reactant after the hydrogel-enzyme construct is exposed to a high temperature condition in a range between 40° C. and 450° ° C., the enzymatic reaction on the organophosphate reactant by individual enzyme molecules embedded within the hydrogel occurring at a residual activity of between about 64% and 100%.

13. A hydrogel-enzyme construct for performing high temperature enzymatic reaction on an organophosphate reactant, the hydrogel-enzyme construct comprising:
a silicon wafer;
a layer of poly(glycidyl methacrylate) (PGMA) in contact with a surface of the silicon wafer;
a hydrogel having multiple layers of a poly(methacrylic acid) (PMAA) polymer in contact with the layer of PGMA; and
a plurality of phosphotriesterase molecules,
wherein adjacent hydrogel polymer layers are connected via cross-linking,
individual phosphotriesterase molecules are embedded between adjacent hydrogel polymer layers,
individual phosphotriesterase molecules are covalently bonded with respective individual hydrogel polymer layers, and
the hydrogel-enzyme construct is capable of performing enzymatic reaction on the organophosphate reactant after the hydrogel-enzyme construct is exposed to a high temperature condition of up to 550° C., the enzymatic reaction on the organophosphate reactant by individual enzyme molecules embedded within the hydrogel occurring at a residual activity of between 20% and 100%,
wherein the plurality of phosphotriesterase molecules comprise Protein Repair One Stop Shop (PROSS) stabilized PTE S5 from *Pseudomonas diminuta* S5 variant (dPTE2), and the organophosphate reactant is paraoxon.

14. The hydrogel-enzyme construct according to claim 13, wherein the silicon wafer comprises a layer of silicon oxide on the surface, the silicon oxide comprises —OH groups which operate to secure the PGMA layer to the silicon wafer, and the PMAA polymer is secured to the PGMA layer by covalent bonding.

15. The hydrogel-enzyme construct according to claim 13, wherein the dPTE2 is obtained from Addgene plasmid #111634 (SEQ ID NO: 1).

* * * * *